(12) United States Patent
Adam et al.

(10) Patent No.: US 11,911,748 B1
(45) Date of Patent: Feb. 27, 2024

(54) MODIFIED HOMOGENEOUS DINUCLEAR TRANSITION METAL-ORGANIC FRAMEWORKS

(71) Applicant: King Faisal University, Al-Ahsa (SA)

(72) Inventors: Mohamed Shaker Sayed Adam, Al-Ahsa (SA); Ahmed Khalil, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/116,150

(22) Filed: Mar. 1, 2023

(51) Int. Cl.
*B01J 31/16* (2006.01)
*B01J 31/24* (2006.01)
*B01J 37/12* (2006.01)

(52) U.S. Cl.
CPC ....... *B01J 31/1625* (2013.01); *B01J 31/2404* (2013.01); *B01J 37/12* (2013.01); *B01J 2531/005* (2013.01)

(58) Field of Classification Search
CPC .............................. B01J 31/2404; B01J 37/12
See application file for complete search history.

(56) References Cited

U.S. PATENT DOCUMENTS

| | | |
|---|---|---|
| 3,853,754 A | 12/1974 | Gosser |
| 2021/0403634 A1 | 12/2021 | Kropp et al. |

FOREIGN PATENT DOCUMENTS

| | | |
|---|---|---|
| EP | 1813258 A2 | 8/2007 |

OTHER PUBLICATIONS

Nami et al., Journal of Sulfur Chemistry, (2017), 38(3), p. 279-290.*
Dragancea, D., et al., "Vanadium(V) Complexes with Substituted 1,5-bis(2-hydroxybenzaldehyde)carbohydrazones and Their Use as Catalyst Precursors in Oxidation of Cyclohexane," Inorganic Chemistry 55: pp. 9187-9203 (Aug. 26, 2016).

* cited by examiner

*Primary Examiner* — Yong L Chu
(74) *Attorney, Agent, or Firm* — Nath, Goldberg & Meyer; Richard C. Litman

(57) ABSTRACT

A dinuclear vanadyl-diisatin succinyldihydrazone complex (VO-diisatin succinyldihydrazone complex), a method of using the dinuclear vanadyl-diisatin succinyldihydrazone complex, and a method of making the dinuclear vanadyl-diisatin succinyldihydrazone complex are provided. The dinuclear vanadyl-diisatin succinyldihydrazone complex has improved catalytic effectiveness and increased efficiency by reducing catalytic reaction time and temperature.

9 Claims, 7 Drawing Sheets

MODIFIED HOMOGENEOUS DINUCLEAR TRANSITION METAL-ORGANIC FRAMEWORKS

BACKGROUND

1. Field

The disclosure of the present patent application relates to modified homogeneous dinuclear transition-metal-organic frameworks, such as a VO-diisatin succinyldihydrazone complex formed from a diisatin succinyldihydrazone ligand. Additionally, the present application involves economizing consumed catalysts for chemical transformation industrial processes with modified homogeneous dinuclear transition metal-organic frameworks.

2. Description of the Related Art

Catalytic processes are of paramount importance in the chemical industry. Homogeneous catalysts are of great interest for synthesizing fine-chemical/specialty chemical/medical and pharmaceutical products for their advantages of high activity and modified chemo, stereo- and regio-selectivity. Most recent chemical transformation consumes high energy amounts for such selective productivity. However, the reusability and high separability of homogeneous metal-organic framework catalysts in the catalytic systems are difficult, as the consumption energy for such catalytic systems is low compared to the heterogamous protocols. Accordingly, the design of novel and more effective homogeneous metal-organic framework catalysts is an essential demand in the industrial fields.

Catalytic reactivity of the homogeneous metal-organic framework catalysts is influenced by the nature of both central metal ions and the coordinated backbone ligands. The effect of the central metal ion could be observed within its ability to approach the reacting components to achieve the catalytic processes to the selective productivity. The role of the donor centers of the coordinated backbone ligand could enhance the catalytic efficacy of the metal-organic framework catalysts. For example, most catalytic oxidation reactions of alcohols, especially benzyl alcohol, need high reaction temperatures (50-90° C.) and take a longer than desired time (3-7 h).

Therefore, metal-organic framework catalysts that enhance the catalytic effectiveness of the catalyst reaction by reducing the consumed time and temperature to room temperature with fewer hours required for the reaction are desired, as is a lower cost synthetic process of such a catalyst.

SUMMARY

The present subject matter relates to modified homogeneous dinuclear transition-metal-organic frameworks such as a VO-diisatin succinyldihydrazone complex from a novel diisatin succinyldihydrazone ligand. Additionally, the present subject matter involves economizing consumed catalysts for chemical transformation industrial processes with modified homogeneous dinuclear transition metal-organic frameworks, as well as a method of synthesizing a novel homogeneous catalyst with high catalytic efficiency, specifically in the novel oxidation of various alcohols, including by way of non-limiting example benzyl alcohol, or thiophene-2,5-diamine, under green conditions.

In one embodiment, the present subject matter may relate to the synthesis and characterization of a diisatin succinyldihydrazone ligand from succinyldihydrazide condensed with isatin. The novel ligand can be characterized using at least $^1$HNMR spectra and $^{13}$CNMR spectra of the ligand.

In an embodiment, the present subject matter may relate to the design, synthesis and characterization of a modified homogeneous dinuclear transition-metal-organic frameworks such as a novel VO-diisatin succinyldihydrazone complex, which is synthesized from the diisatin succinyldihydrazone ligand blended with VO(acac)$_2$ (vanadyl acetylacetonate). The novel catalyst is characterized using IR, UV-Vis, mass spectra, and elemental analysis and magnetism.

In this regard, an embodiment of the present subject matter relates to a diisatin succinyldihydrazone ligand having the following structure

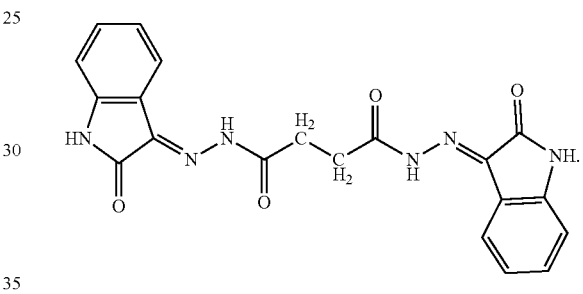

In another embodiment, the present subject matter relates to a method of making the diisatin succinyldihydrazone ligand, the method comprising condensing succinyl dihydrazide with isatin to form the diisatin succinyldihydrazone ligand.

In a further embodiment, the present subject matter relates to a VO-diisatin succinyldihydrazone complex, said complex having the following structure:

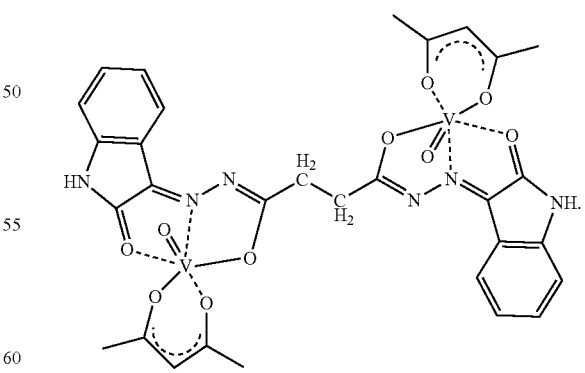

In another embodiment, the present subject matter relates to a method of making the VO-diisatin succinyldihydrazone complex,
the method comprising mixing a diisatin succinyldihydrazone ligand having the following structure

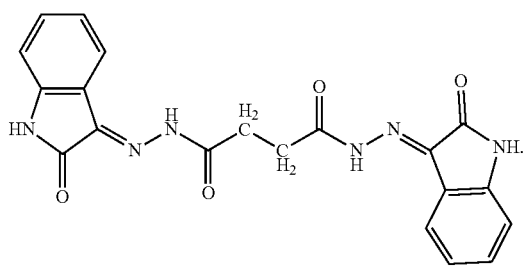 [SMILES: O=C(CCC(=O)N/N=C1/C(=O)Nc2ccccc21)N/N=C1/C(=O)Nc2ccccc21]

with VO(acac)$_2$ (vanadyl acetylacetonate) in methanol to form the VO-diisatin succinyldihydrazone complex by the following reaction scheme:

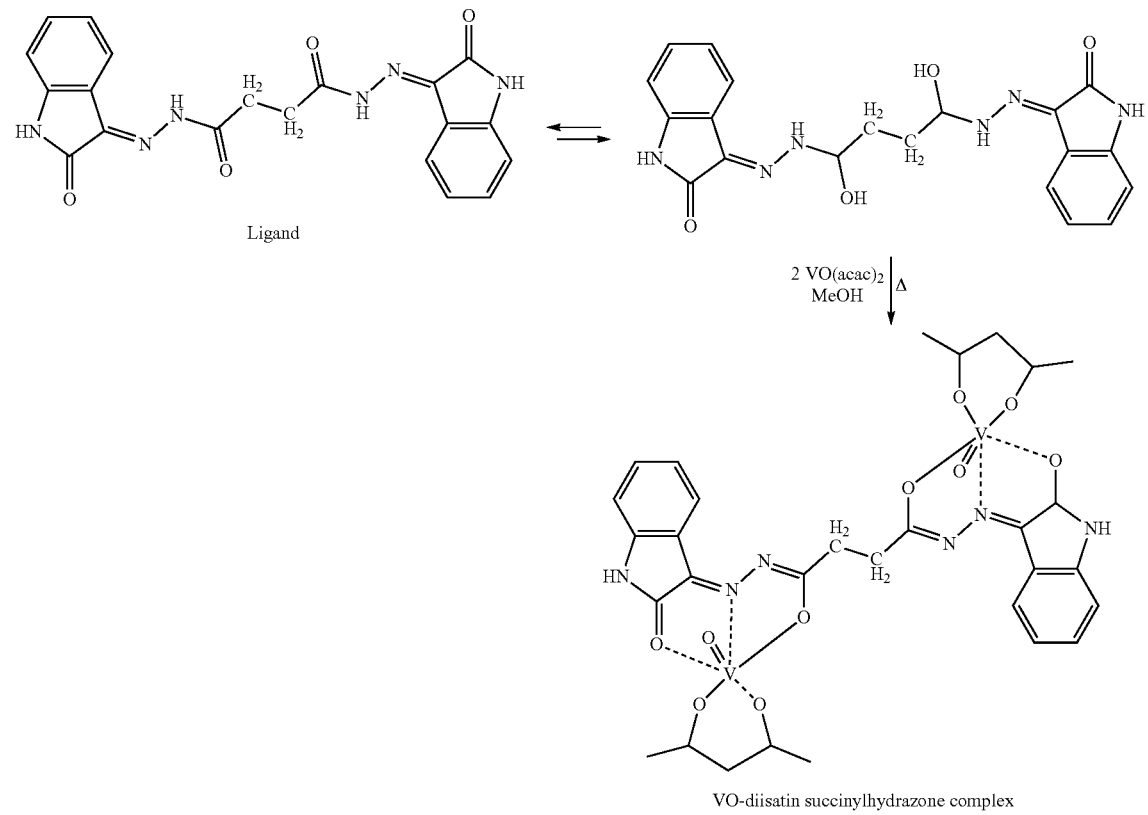

VO-diisatin succinylhydrazone complex

In yet another embodiment, the present subject matter relates to a method of catalyzing aerobic oxidation of an alcohol, the method comprising: contacting the VO-diisatin succinyldihydrazone complex as described herein with the alcohol in the presence of aqueous H$_2$O$_2$; and obtaining a corresponding aldehyde and acid, wherein the VO-diisatin succinyldihydrazone complex reduces the time and the temperature required to carry out the aerobic oxidation of the alcohol.

Similarly, another embodiment of the present subject matter relates to a method of catalyzing aerobic oxidation of thiophene-2,5-diamine, the method comprising: contacting the VO-diisatin succinyldihydrazone complex catalyst as described herein with the thiophene-2,5-diamine in the presence of aqueous H$_2$O$_2$ at room temperature; and obtaining a corresponding 2,5-dinitrosothiophene-1-oxide.

In an embodiment, the present subject matter may relate to economizing consumed catalysts for chemical transformation industrial processes with modified homogeneous dinuclear transition metal-organic frameworks having high catalytic efficiency, including in the oxidation of an alcohol or thiophene-2,5-diamine under green conditions.

These and other features of the present subject matter will become readily apparent upon further review of the following specification.

DETAILED DESCRIPTION OF THE PREFERRED EMBODIMENTS

Figure 1A:
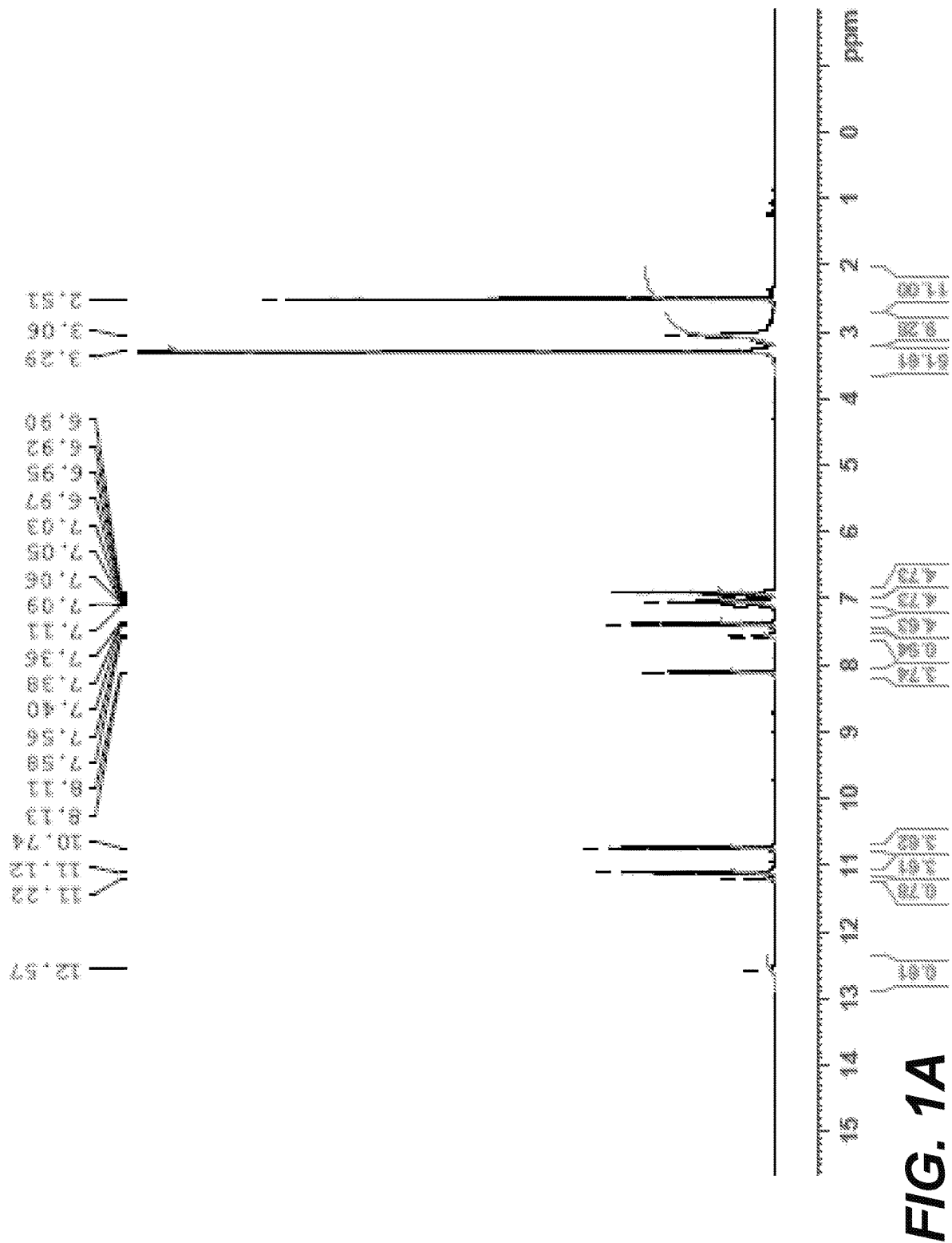
FIG. 1A is an $^1$HNMR spectra of the diisatin succinyldihydrazone ligand in DMSO-d6 at 25° C.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to modified homogeneous dinuclear transition-metal-organic frameworks such as a VO-diisatin succinyldihydrazone complex formed from a novel diisatin succinyldihydrazone ligand. Additionally, the present subject matter relates to economizing consumed catalysts for chemical transformation industrial processes with said modified homogeneous dinuclear transition metal-organic frameworks, as well as a method of synthesizing a novel homogeneous catalyst with high catalytic efficiency, including in the oxidation of alcohols, such as, by way of non-limiting example, benzyl alcohol, and/or thiophene-2, 5-diamine under green conditions.

According to the present subject matter, the role of the donor centers of the coordinated backbone ligand may enhance the catalytic efficacy of the metal-organic framework catalysts. Use of dinuclear central metal ions instead of a mononuclear central metal ion in the metal-organic framework catalysts may enhance the catalytic effectiveness of the catalyst by reducing the consumed time to a few hours and the temperature to room temperature.

Regarding modified homogeneous dinuclear transition-metal-organic frameworks such as a VO-diisatin succinyldihydrazone complex from a novel diisatin succinyldihydrazone ligand, the role of the donor centers of the coordinated backbone ligand may enhance the catalytic efficacy of the metal-organic framework catalysts. Use of dinuclear central metal ions instead of a mononuclear central metal ion in the metal-organic framework catalysts may enhance the catalytic effectiveness of the catalyst by reducing the consumed time to a few hours and the temperature to room temperature.

In one embodiment, the present subject matter may relate to the synthesis and characterization of a diisatin succinyldihydrazone ligand from succinyldihydrazide condensed with isatin. The novel ligand can be characterized using $^1$HNMR spectra and $^{13}$CNMR spectra of the ligand.

Synthesis of Diisatin Succinyldihydrazone Ligand

In this regard, an embodiment of the present subject matter relates to a diisatin succinyldihydrazone ligand having the following structure In an embodiment, this ligand is effective for enhancing catalytic effectiveness of a VO complex catalyst reaction by reducing consumed time and temperature when said ligand is combined with, e.g., vanadyl acetylacetonate.

In another embodiment, the present subject matter relates to a method of making the diisatin succinyldihydrazone ligand, the method comprising condensing succinyl dihydrazide with isatin to form the diisatin succinyldihydrazone ligand according to Scheme 1:

Scheme 1. Synthetic pathway of the novel ligand from succinyl dihydrazide

In certain embodiments in this regard, the succinyl dihydrazide is condensed with isatin in the presence of methanol. In additional embodiments, the production method can further comprise condensing the succinyl dihydrazide in methanol with the isatin in methanol by mixing to form a methanolic mixture, and refluxing the methanolic mixture with stirring for about 4 hours at about 80° C. In other embodiments, the refluxing and stirring can occur for at least about 4 hours, for about 3 to about 5 hours, or for any time amount therein. In certain other embodiments, the refluxing and stirring can occur at a temperature of at least about 80° C., at about 70° C. to about 90° C., or at any temperature therein. In a further embodiment, the production method can further comprise removing the methanol from the methanolic mixture by filtration and recrystallizing a solid precipitate in methanol to produce a yellow powder of the diisatin succinyldihydrazone ligand.

Synthesis of VO-Diisatin Succinyldihydrazone Complex

In an embodiment, the present subject matter may relate to the design, synthesis and characterization of a modified homogeneous dinuclear transition-metal-organic frameworks such as a novel VO-diisatin succinyldihydrazone complex, which is synthesized from the diisatin succinyldihydrazone ligand blended with VO(acac)$_2$ (vanadyl acetylacetonate). The novel catalyst is characterized using IR, UV-Vis, mass spectra, and elemental analysis and magnetism.

In this regard, an embodiment of the present subject matter relates to a VO-diisatin succinyldihydrazone complex, said complex having the following structure:

In another embodiment, the present subject matter relates to a method of making the VO-diisatin succinyldihydrazone complex, the method comprising mixing a diisatin succinyldihydrazone ligand having the following structure with VO(acac)$_2$ (vanadyl acetylacetonate) in methanol to form the VO-diisatin succinyldihydrazone complex by the following reaction Scheme 2:

Scheme 2. VO-diisatin succinyldihydrazone complex formation from the coordination of ligand with VO2+ ion in methanolic media.

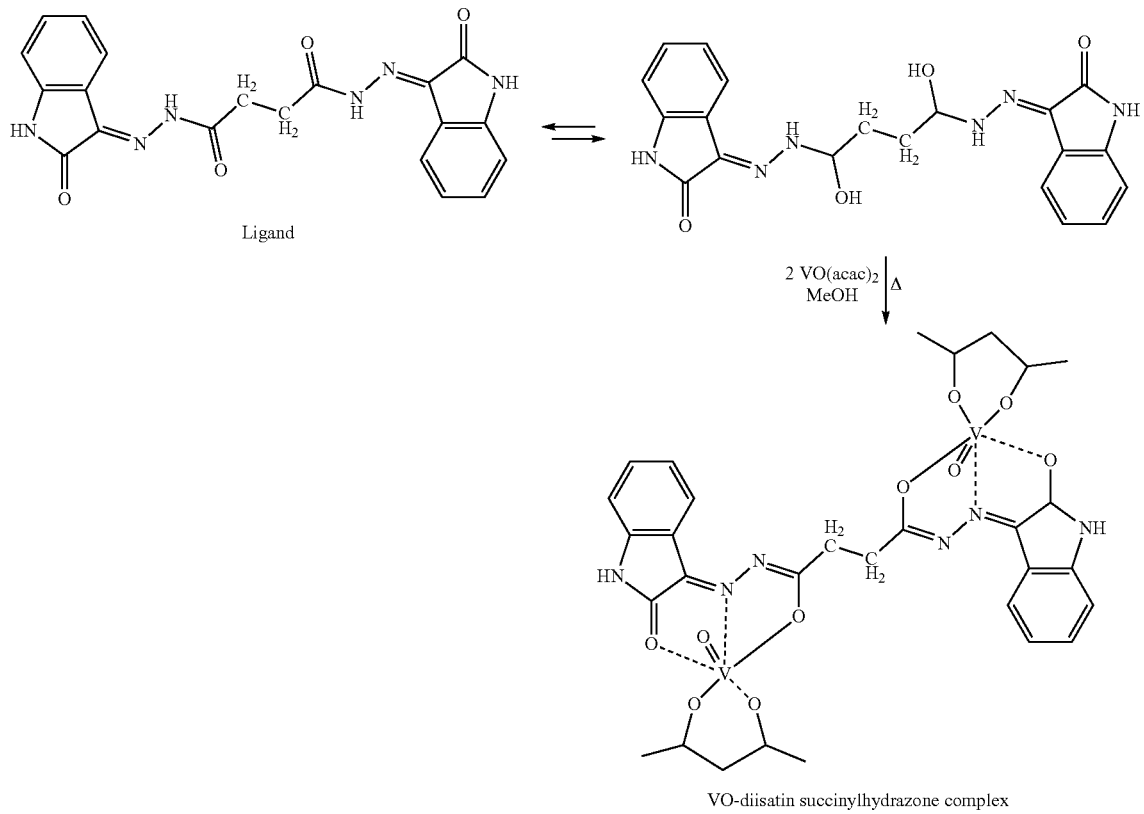

VO-diisatin succinylhydrazone complex

In certain embodiments in this regard, the diisatin succinyldihydrazone ligand in methanol is poured into the VO(acac)$_2$ (vanadyl acetylacetonate) in methanol to form a complexing reaction mixture, and the mixture is stirred and refluxed for about 4 h at about 80° C. In other embodiments, the refluxing and stirring can occur for at least about 4 hours, for about 3 to about 5 hours, or for any time amount therein. In certain other embodiments, the refluxing and stirring can occur at a temperature of at least about 80° C., at about 70° C. to about 90° C., or at any temperature therein. In additional embodiments, the production method can further comprise bubbling nitrogen (N$_2$) gas through the complexing reaction mixture, extracting MeOH from the complexing reaction mixture to produce a solid complex, and aggregating the solid complex by washing with diethyl ether to produce an aggregated solid complex. In still further embodiments, the production method can further comprise recrystallizing the aggregated solid complex in methanol to obtain the VO-diisatin succinyldihydrazone complex as a powder.

Methods of Catalytic Oxidation

In an embodiment, the present subject matter may relate to economizing consumed catalysts for chemical transformation industrial processes with modified homogeneous dinuclear transition metal-organic frameworks having high catalytic efficiency, including in the novel oxidation of an alcohol, and thiophene-2,5-diamine under green conditions.

Aerobic oxidation of alcohols is one of the most important methods for producing aldehydes. The effective oxidation of alcohols must exhibit certain types of chemical selectivity, such as the selective oxidation of primary alcohols to aldehydes without overoxidation to carboxylic acids. Developing and designing efficient catalytic systems and reactors is the key to the effective oxidation of alcohol.

Accordingly, in another embodiment, the present subject matter relates to a method of catalyzing aerobic oxidation of an alcohol, the method comprising: contacting the VO-diisatin succinyldihydrazone complex as described herein with the alcohol in the presence of aqueous H$_2$O$_2$; and obtaining a corresponding aldehyde and acid, wherein the VO-diisatin succinyldihydrazone complex reduces the time and the temperature required to carry out the aerobic oxidation of the alcohol. In certain non-limiting embodiments, the alcohol can be benzyl alcohol, the aldehyde can be benzaldehyde, and the acid can be benzoic acid. In further embodiments, an about 90% yield of the benzaldehyde, or greater, is obtained.

Most of catalytic oxidation reactions of alcohols, especially benzyl alcohol, need high reaction temperature (50-120° C.) and consume a long time (3-7 h) to progress. The catalytic effectiveness of the dinuclear vanadyl-diisatin succinyldihydrazone complex catalyst, in contrast, is affirmed as this complex requires a significantly less catalytic amount, by way of non-limiting example, about 0.005 mmol, in the oxidation of benzyl alcohol (about 1.0 mmol) with optimization conditions (25° C. after 1.5 h) under solvent-free atmosphere. The obtained results could support the high catalytic action of dinuclear vanadyl-diisatin succinyldihydrazone complex catalysts, in which the coordinated ligand could behave as a redox-active ligand, in industrial fields with less required temperature and consumed time. Using vanadyl ion as the transition metal ion is most favorable due to the interesting catalytic characteristics of the high valent vanadium ion. In certain embodiments, the catalytic oxidation of thiophene-2,5-diamine by using $H_2O_2$ as the greenest oxidant and catalyzed by homo dinuclear vanadyl-diisatin succinyldihydrazone complex catalyst is accomplished at room temperature after 40 min.

Similarly, another embodiment of the present subject matter relates to a method of catalyzing aerobic oxidation of thiophene-2,5-diamine, the method comprising: contacting the VO-diisatin succinyldihydrazone complex catalyst as described herein with the thiophene-2,5-diamine in the presence of aqueous $H_2O_2$ at room temperature; and obtaining a corresponding 2,5-dinitrosothiophene-1-oxide. In certain embodiments, an about 33% yield of the 2,5-dinitrosothiophene-1-oxide is obtained.

EXAMPLES

Example 1: Production of the Diisatin Succinyldihydrazone Ligand

From Sigma-Aldrich and Merck, all the necessary initial materials and precursors were employed without any re-handling assigned. 0.73 g of succinyl dihydrazide (1) (5 mmol in 30 mL of methanol (MeOH)) was condensed with 1.47 g of isatin (10 mmol) in 50 mL methanol by a leisure mixing. The acquired methanolic mixture was refluxed with stirring for 4 hours (at 80° C.). The reaction progress was followed by TLC. The organic solvent was removed by filtration. The solid precipitate was recrystallized in MeOH to afford pure yellow powder of diisatin succinyldihydrazone ligand, yielding almost 1.64 g (81%).

Evaluation of the nuclear magnetic resonances' spectra (hydrogen and carbon nuclei) in DMSO-d6 at 25° C. for the ligand was achieved using Bruker FT-NMR multinuclear spectrometric device (model of ARX400). The magnetic fields for carbon nuclei and hydrogen protons were 100.6 and 400.1 MHz, respectively.

3.06 (s, 4H, $C_2H_4$), 6.91 (d, $^3J$=7.2 Hz, 2H), 7.05 (t, $^4J$=2.0 and $^3J$=7.0 Hz, 2H), 7.38 (t, $^3J$=7.3 Hz, 2H), 8.12 (d, $^3J$=7.0 Hz, 2H), 10.74 (s, 2H, NH) and 11.12 ppm (s, 2H, NH) (FIG. 1A); (for the dienolic form): 6.96 (d, $^3J$=7.1 Hz), 7.09 (t, $^4J$=1.9 and $^3J$=7.0 Hz), 7.57 (d, $^3J$=6.9 Hz), 11.22 (s, OH) and 12.57 ppm (s, NH).

Figure 1B:
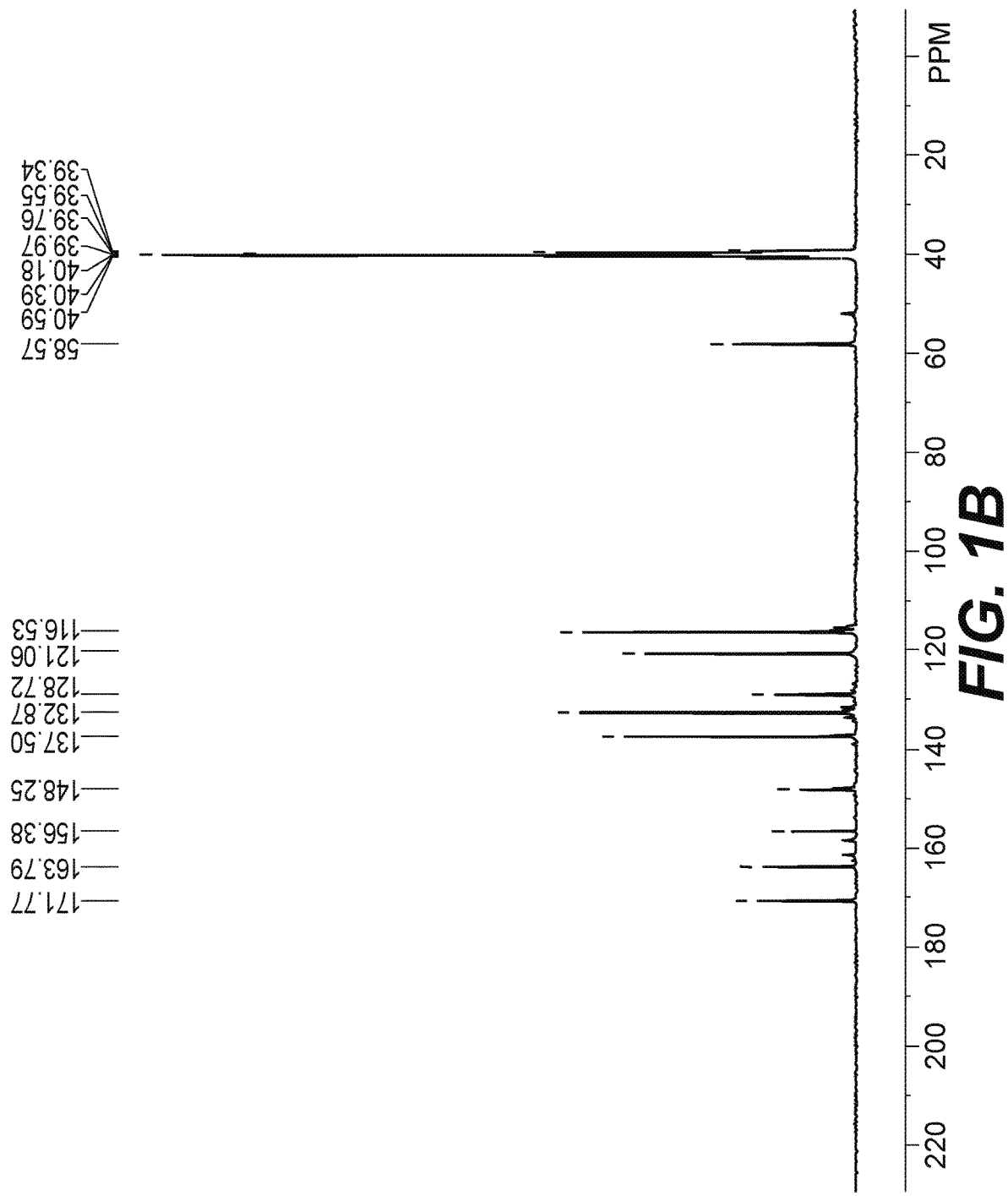
FIG. 1B is a $^{13}$CNMR spectra of the diisatin succinyldihydrazone ligand in DMSO-d6 at 25° C.

$^{13}$CNMR spectra of the diisatin succinyldihydrazone ligand: 58.57 ($CH_2$), 116.53 (CH), 121.06 (CH), 128.72 (Cq), 132.87 (CH), 137.50 (CH), 148.25 (Cq), 156.38 (Cq), 163.79 ($C_q$, C=N) and 191.77 ppm (Cq, C=O) (FIG. 1B).

Figure 2:
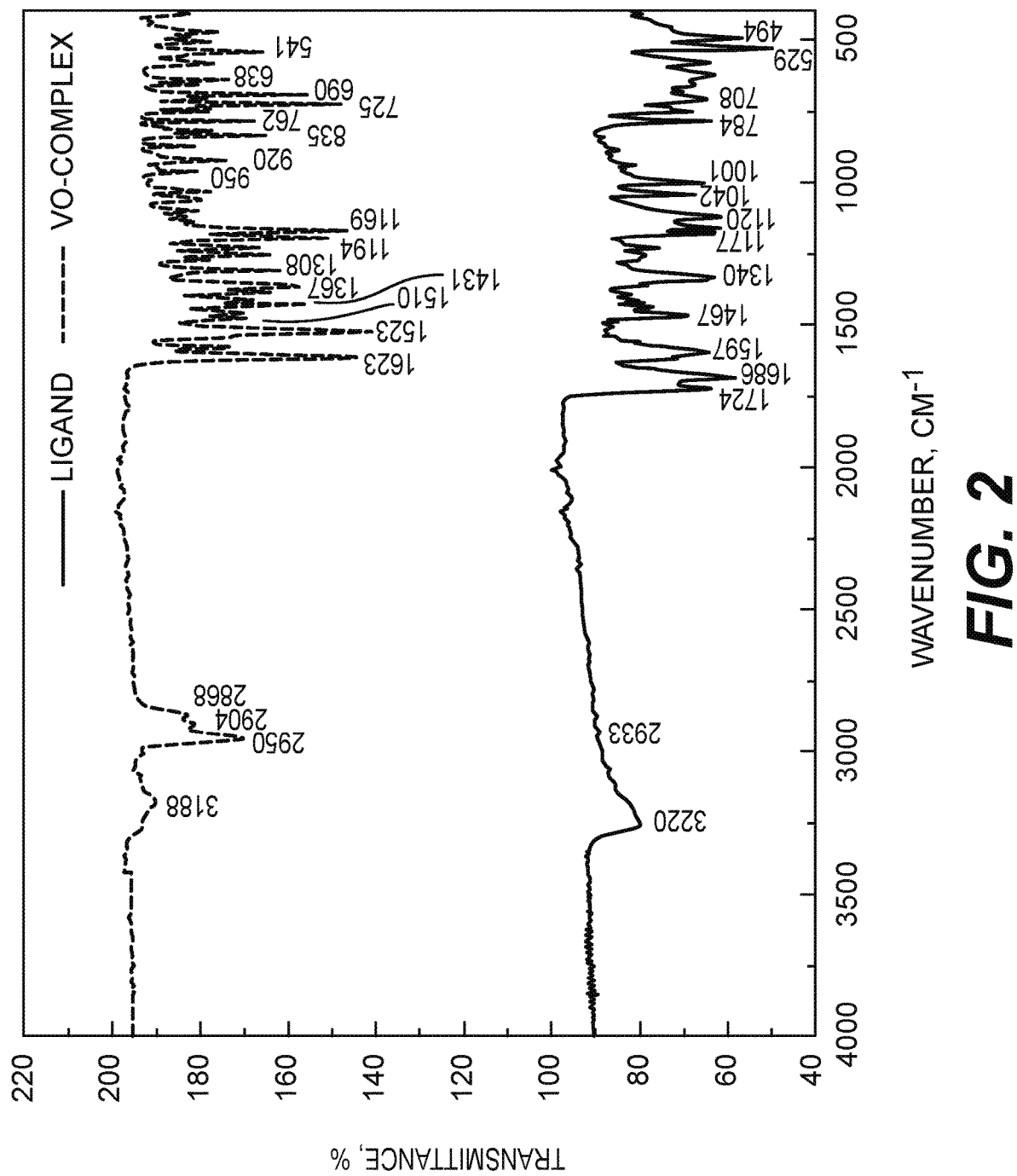
FIG. 2 shows comparable FT-IR spectral scans for the solid phase of the diisatin succinyldihydrazone ligand and the VO-diisatin succinyldihydrazone complex at 25° C.

FTIR spectra of the free ligand: 3220 (NH), 1724 (C=O), 1686 (C=O) and 1597 cm$^{-1}$ (C=N) (FIG. 2).

Example 2: Production of the VO-Diisatin Succinyldihydrazone Complex 2.0 mmol of diisatin succinyldihydrazone ligand (0.81 g) in methanol (40 mL) was poured leisurely to VO(acac)$_2$ (vanadyl acetylacetonate, 1.06 g) in 50 mL MeOH. The complexing reaction took place by stirring and reflux the reaction mixture for 4 h (at 80° C.). TLC technique was applied to monitor the accomplishment of the reaction. With $N_2$ gas bubbling through the reaction solution of the complexation of the VO-diisatin succinyldihydrazone complex, the coordination of the ligand to $VO^{2+}$ ion was taken place, avoiding a possible air oxidation of VO(IV) to VO(V) ion. Finally, after the completion, MeOH was extracted by a reduced pressure. The acquired solid complex was aggregated with careful washing with diethyl ether several times. A processing of recrystallization was achieved in MeOH to obtain a clear colored powder complex. The yielded amount of the VO-diisatin succinyldihydrazone complex was 1.04 g with 70%. The decomposition point for the VO-diisatin succinyldihydrazone complex was 286° C. (Scheme 2).

FTIR spectra of the VO-diisatin succinyldihydrazone complex: 3188 (NH), 1623 (C=O), 1510 (C=N), 1431 (C=N), 2950, 2904, 2868 and 1523 (acetylacentone group), 835 (V=O), 725 (V-O), 690 (V-O) and 541 cm-1 (V-N) (FIG. 2).

The decomposition/melting point determination of the VO-complex was measured by using a Gallenkamp (Sanyo) machine. Hence, the melting point is 221° C.

Example 3: Structural Confirmations

Confirming the diisatin succinyldihydrazone ligand and its corresponding VO-complex chemical structures was conducted by the analyses of mass, ultraviolet-visible, and infrared spectral studies. Also, the CHN analyses (i.e., EA, elemental analyses), conductance characteristics, and magnetic features were studied and are shown in Table 1.

TABLE 1

| Comp. (M.W.) | Color | CHN analyses, % | | | Electronic spectra | | | $\Lambda_m$, $\Omega^{-1}$ cm$^2$ mol$^{-1}$ | |
|---|---|---|---|---|---|---|---|---|---|
| | | C | H | N | $\lambda$max, nm | $\varepsilon$, mol$^{-1}$·cm$^{-1}$ | Assign. | DMSO | DMF |
| $H_2LC_2$ (404.39 g·mol$^{-1}$) | Yellow | 59.81 (59.90) | 4.31 (3.99) | 20.56 (20.78) | 262 338 | 13285 5179 | $\pi\to\pi^*/n\to\pi^*$ LCT | 27 | 33 |
| VOLC$_2$ (734.47 g·mol$^{-1}$) | Dark green | 48.68 (48.66) | 4.21 (4.63) | 11.64 (11.35) | 258 353 386 520 | 5283 4867 4702 2016 | $\pi\to\pi^*$ n$\to\pi^*$ L-MCT d$\to$d | 29 | 40 |

Table 1 shows the main elements percentage analyses (CHN, %) of the ligand and VO-diisatin succinyldihydrazone complex. The ultraviolet-visible spectra of both compounds in DMF (1.0×10$^{-5}$ mol·dm$^{-3}$) and the conductivity measurements ($\Delta_m$, $\Omega^{-1}$·cm$^2$·mol$^{-1}$) are in DMSO and DMF (1.0× 10$^{-3}$ mol·dm$^{-3}$) at ambient temperature.

Figure 3:
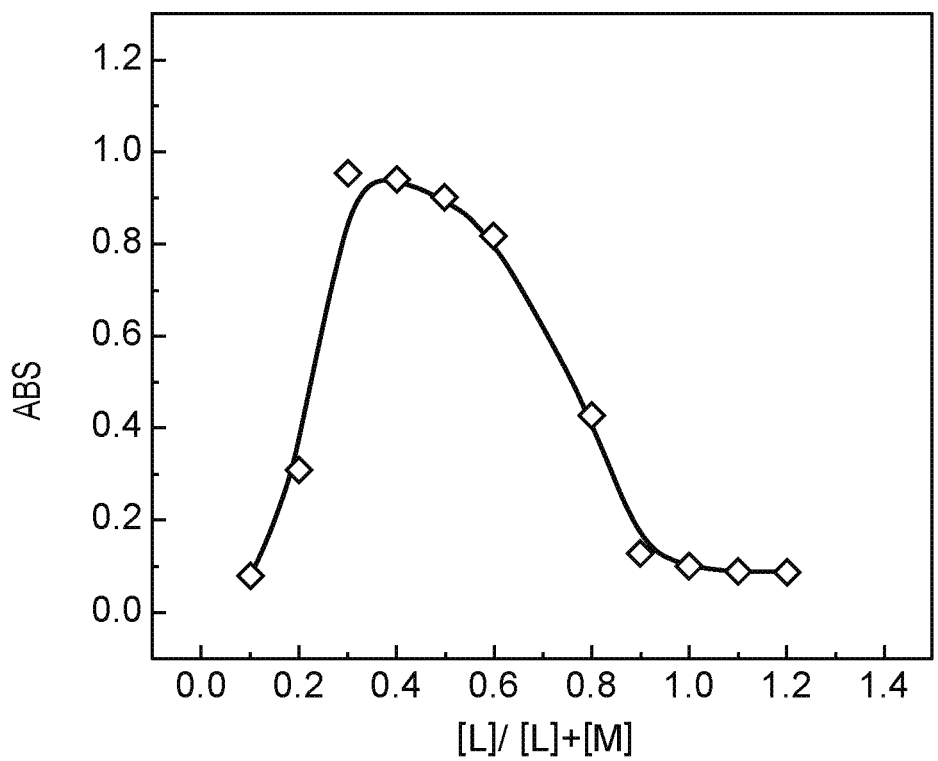
FIG. 3 is a continuous variation plot of the stoichiometric molar ratios for the complexation of the diisatin succinyldihydrazone ligand to VO$^{2+}$ ion in DMF media at [L] (ligand)=[M$^{2+}$] (VO$^{2+}$ ion)=1×10$^{-5}$ mol dm$^{-3}$ at 25° C.

At ambient temperature, C, H, N (the main elements in the current compounds) percentages are estimated within the GMBH varioEl device (model of V2.3). The main elements analyses of CHN are aimed at determining the purity form of all current compounds, which are listed in Table 1. The considered percentages of the main elements analyses are harmonic with the planned ones with less than 0.4% difference for the diisatin succinyldihydrazone ligand and its VO-diisatin succinyldihydrazone complex. Notably, the high-purity form of such results could be deduced with a confirmation of their chemical structures (Scheme 1). The melting point for the diisatin succinyldihydrazone ligand and the decomposition degree for the VO-diisatin succinyldihydrazone complex are 221 and 286° C., respectively, attributing to their high stability with a distinguished variation in that point between the free ligand and its VO-diisatin succinyldihydrazone complex. Such observation is displayed for the complexing influence of the high stability of VO-diisatin succinyldihydrazone complex compared to its uncoordinated ligand. The stoichiometric ratios of the diisatin succinyldihydrazone ligand to the coordinated $VO^{2+}$ ions are tested in DMF through the spectrometric continuous variation method. From FIG. 3, the coordination features of the diisatin succinyldihydrazone ligand to $VO^{2+}$ ions are found in 1:2 molar amounts, respectively (Scheme 2).

Figure 4:
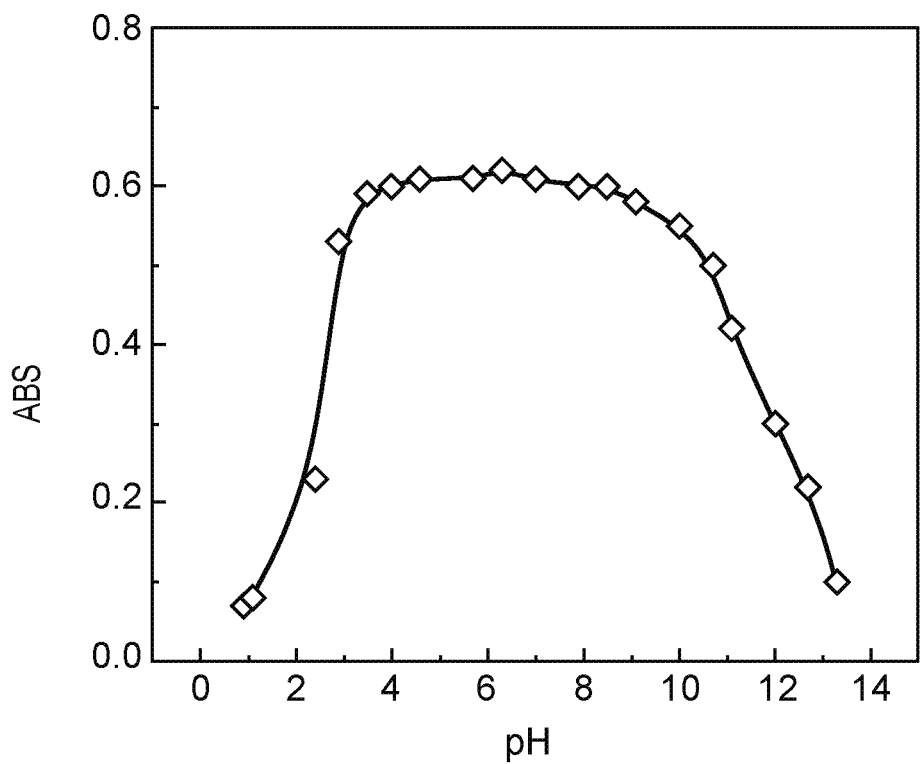
FIG. 4 is a plot showing pH affect stability of a DMF solution of the VO-diisatin succinyldihydrazone complex.

Moreover, the stability of the VO-diisatin succinyldihydrazone complex at a wide range of pH values was investigated spectroscopically within the standard universal buffer solutions. The VO-diisatin succinyldihydrazone complex elucidated an illustrated stability area from a pH of 3.1 to 10.9 (FIG. 4).

Particularly, the diisatin succinyldihydrazone ligand and its VO-diisatin succinyldihydrazone complex were remarkably soluble in the organic solvents with high coordinating characteristics, e.g., N,N'-dimethylformamide (DMF) and dimethylsulfoxide (DMSO). The VO-diisatin succinyldihydrazone complex showed a hard dissolution in polar organic solvents, i.e., slight solubility, in acetonitrile, ethanol, acetone and methanol. The molar conductivity of the new compounds ($1.0\times10^{-3}$ mol $dm^{-3}$) was studied in N,Ndimethylformamide (DMF), and dimethyl sulfoxide (DMSO) by Jenway conductivity meter apparatus at 25° C. The noted minimal solubility of VO-diisatin succinyldihydrazone complex was attributed to its low conductivity measurements, as given in Table 1, in DMF and DMSO. Such behavior could be considered for the covalent nature of VO-diisatin succinyldihydrazone complex. Additionally, VO-diisatin succinyldihydrazone complex referred to its para-magnetic features with 2.29 B.M. due to the one unpaired electron of $V^{4+}$ ion in 3d orbitals, i.e., $3d^1$.

NMR Spectra

The deuterated solutions of the diisatin succinyldihydrazone ligand in DMSO-d6 at the ambient temperature, the NMR spectra (nuclear magnetic resonance spectroscopy) for the 1-hydrogen and 13-carbon nuclei in the free diisatin succinyldihydrazone ligand were examined and are given in FIGS. 1A and 1B. The succinyl group's four protons are located at 4.56 ppm in the ligand. The two NH protons of the dihydazone and diisatin moieties in the ligand are found at 11.12 and 10.74 ppm (as broad signal in the diketo form) (Scheme 1). The other spectral signals for the ligand have belonged to the two aryl rings of the two isatin moieties, which have no observable shifts after the complexation of its ligand (FIG. 1A). The dienolic tautomer could be observed by NMR spectra as a minor form. The HNMR spectra for the ligand solution (FIG. 1A) represented small absorption signals beside the main reported ones in the experimental section, which referred to the dienolic tautomer. At 12.57 ppm, a small signal was observed which assigned for the NH proton of the isatin moiety. The OH proton of the dienolic tautomer could be distinguished at 11.22 ppm. Moreover, the other aryl protons showed spectral signals at 6.96, 7.09 and 7.57 ppm.

For the absorption spectra of carbon nuclei for the free ligand, the hydrazone chain's two carbonyl groups (C=O) show their carbon spectral signal at 171.77 ppm (FIG. 1B) in the diketo form. The free ligand's carbon spectral signal of C=N is detected at 163.79 ppm. Additionally, in the aliphatic area of the 13CNMR spectra, the carbon signal of the succinyl chain is located at 58.57 ppm for the ligand. The tautomeric form of the dienolic structure could be distinguished clearly by 13 CNMR spectra (FIG. 1B) by small spectral signals. At 162.34, 158.79, 133.90, 131.54, 115.68 and 52.88 ppm, therefore the dienolic structure of the free ligand could be confirmed.

UV and Vis. Spectra

Figure 5:
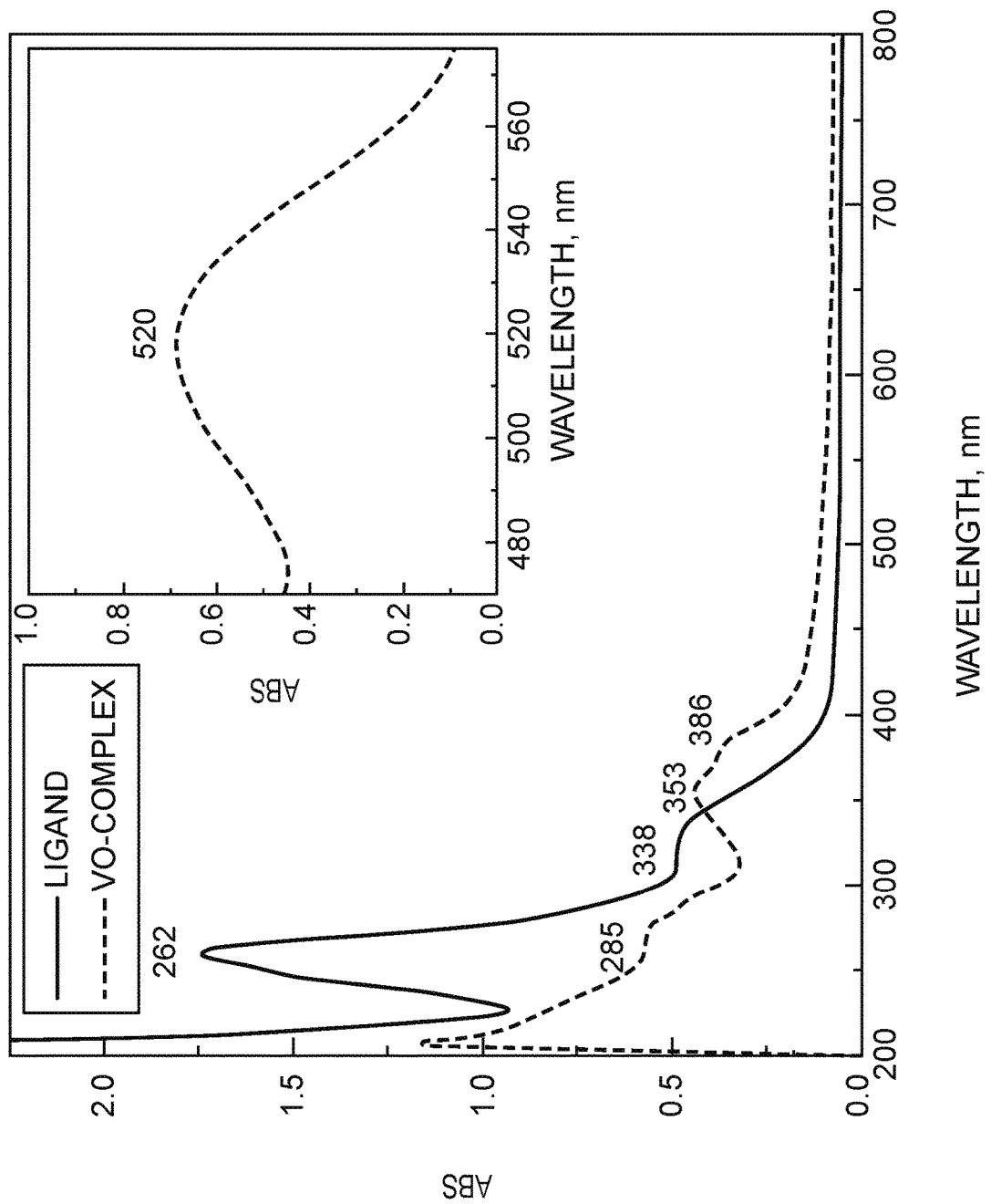
FIG. 5 shows, at 25° C. and in DMF, the ultraviolet and visible spectra for 1.0×10$^{-6}$ mol·dm$^{-3}$ for the diisatin succinyldihydrazone ligand and the VO-diisatin succinyldihydrazone complex at 1.0×10$^{-3}$ mol·dm$^{-3}$.

The ultraviolet visible spectra of the diisatin succinyldihydrazone ligand and VO-complex solutions in DMF ($1.0\times 10^{-6}$ mol·$dm^{-3}$, i.e., diluted, or $1.0\times10-3$, i.e., concentrated solutions) are explored at the ambient temperature through Shimadzu spectrophotometer of UV-1800 model. The DMF solution of the current diisatin succinyldihydrazone ligand and its VO-diisatin succinyldihydrazone complex represents the effect of complexation on the obvious electronic transitions in the diisatin succinyldihydrazone ligand with absorption bands at the maximum wavelength λmax and the derived molar absorptivity (Table 1 and FIG. 5). The observed π→π* and n→π* electronic transitions are distinguished at 262 nm (for the ligand), which little shifted after complexation of the ligand to be observed at 285 and 353 nm (VO-diisatin succinyldihydrazone complex), respectively, in the uncolored area. The current absorption bands are displayed for the electronic transition of the aryl rings π-bonds, >C=O, >C=N— and —NH lone pairs. The charge transfer spectral absorption is located at 338 nm (the free ligand), referring to the change transfer through the ligand molecule), and 386 nm (VO-diisatin succinyldihydrazone complex), assigning for the electron density transfer form $V^{4+}$ ion to the n-orbitals of the coordinated ligand as a charge transfer, in the visible area. An additional broad band at a low energy area is positioned at 520 nm (VO-diisatin succinyldihydrazone complex), which is responsible for the electronic d→d transition, providing the coordination of the ligand molecule to $VO^{2+}$ ion. This band refers to the vanadium ion being charged as +4 with $3d^1$ electronic distributions without any probability of oxidation to the more stable V(V) ion (with $3d^0$) in its coordinated complex.

Infrared Spectral Studies

At ambient temperature, FTIR-spectroscopic scans of the ligand and VO-complex (the solid phase) were examined through FT-IR spectrophotometer Agilent Technology of Cary-630 model device. The samples of the ligand and VO-diisatin succinyldihydrazone complex were measured, and the considered spectral bands are plotted in FIG. 2. The resonating bands of two identical NH bond of the diisatin and hydrazone (the amido group) moieties appeared and overlapped at 3220 $cm^{-1}$, as a broad band. The ligand is found in its diketo form, as the most stable form, as shown in Scheme 1. The two NH stretching band for the diisatin moieties is little shifted after bonding to $VO^{2+}$ ion to be located at 3188 $cm^{-1}$, in VO-diisatin succinyldihydrazone complex (Scheme 2).

The apparent sharp band for the two C=O bands of the two isatin moieties, obtained at 1686 $cm^{-1}$ in the free ligand, are displayed at 1623 $cm^{-1}$ in the VO-diisatin succinyldihydrazone complex. That distinguished shift due to the presence of $VO^{2+}$ ion, which could be considerably assigned for their participation within the oxygen lone pair of C=O for coordination to the metal ion.

For the diketo form, the two carbonyl groups are located at 1742 $cm^{-1}$, which are not found after the complexation of the ligand, as observed for the reported analogues. On the other side, two new imino groups (>C=N—) are appeared in the complexes at 1510 cm$^{-1}$, for VO-diisatin succinyldihydrazone complex. Such behavior could prove the coordination of the deprotonated hydroxyl group of the dienolic structure of the ligand to V$^{4+}$ ion. Furthermore, the sharp band of the two >C=N— groups is observed at 1597 cm$^{-1}$, which shifted to lower wave number values after its coordination to VO$^{2+}$ ion within N-lone pair to be detected at 1431 cm$^{-1}$, VO-diisatin succinyldihydrazone complex. The bond of the aliphatic chain of the coordinated acetylacentone group to V$^{4+}$ ions in VO-diisatin succinyldihydrazone complex could be distinguished by the broad bands at 2950, 2904, 2868, and 1523 cm$^{-1}$. Also, for VO-diisatin 1 succinyldihydrazone complex, the resonating spectral bands for V=O, V-O, V-O, and V-N bonds are located at 835, 725, 690, and 541 cm$^{-1}$, respectively.

Mass Spectra

Figure 6A:
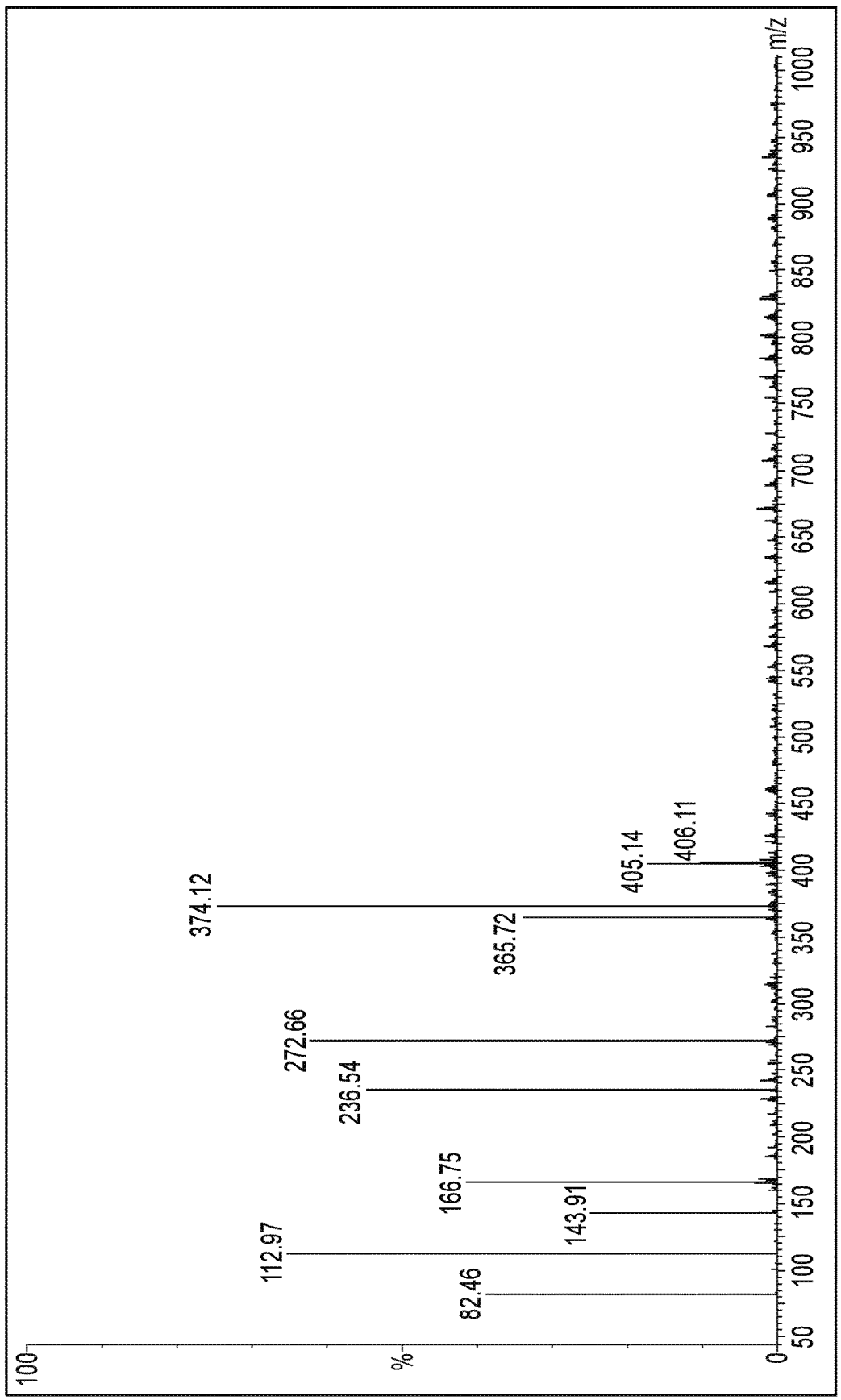
FIG. 6A shows EI-Mass spectra of the diisatin succinyldihydrazone ligand in DMF media at 25° C.
Figure 6B:
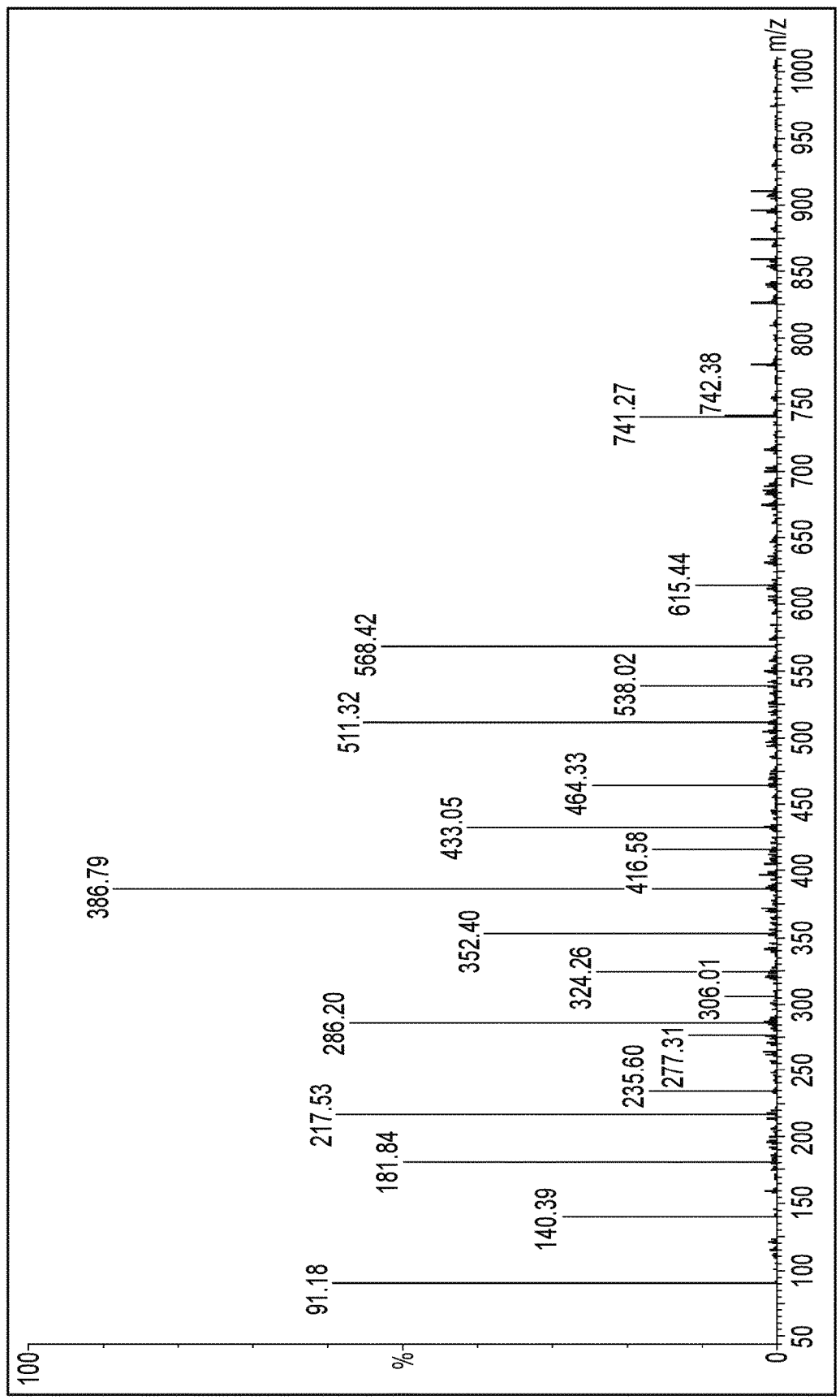
FIG. 6B shows EI-Mass spectra of the VO-diisatin succinyldihydrazone complex in DMF media at 25° C.

MS (m/z) mass spectra for the acetonitrile solutions of the diisatin succinyldihydrazone ligand and VO-complex were obtained by using mass spectrometric apparatus of model Qtof Micro YA263. EI-MS spectral scans with positive modes of analyses for the solutions of the ligand and VO-diisatin succinyldihydrazone complex were investigated and are represented in FIGS. 6A and 6B. The free ligand shows base peaks for the positive mode at 405.14 and 406.11 m/z for the mass fraction of [HL+1], 374.12, 272.66, 166.75, 112.97, and 82.46 m/z (FIG. 6A). On the other hand, the VO-diisatin succinyldihydrazone complex displays base peaks at 742.38 and 741.27 for the mass fraction [ML+1], 568.42, 464.33, 386.79, 306.01, 277.31 and 181.84 m/z for the other mass fraction of the complex molecule (FIG. 6B).

Example 4—Catalytic Oxidation Process of Benzyl Alcohol 0.005 mmol of VO-complex catalyst was poured into 1.0 mmol benzyl alcohol in 10 mL acetonitrile and then stirred for 10 min at the required applicable temperature (from 25 to 40° C.). After that, 3.0 mmol of $H_2O_2$ (solution in water, 30%) was poured drop wise into the above solution under homogenous aerobic conditions. For the catalytic system in $H_2O$, chloroform, or solvent-free conditions, the catalytic reactivity of VO-complex was tested.

By subjecting to a gas chromatography-mass spectrometric device (GC-MS), the % (percentage) of all reaction contents of the reactant, selective products, and other products were evaluated. For the redox system in water, the % percentage of the products were evaluated in GC-MS by their extraction from water to an organic solvent (e.g., ethyl acetate).

The GC-MS device is made up of the Shimadzu model of QP2010 S E. The column parameters are Rxi-5 Sil MS capillary column of 30 m length×0.25 mm ID×0.25 um film thickness. Detection of the catalytic processes products starts with the sample injection at 25° C. of the oven. The oven temperature is progressively improved with the rate of 10° C./min to 200° C. The temperature of the GC-oven is specified for 60 s at 40° C. with the most suitable mode, i.e., splitless mode, and the inlet operation is achieved. The carrier gas is Helium, with a purity of 99.999% and a fluid rate of 1 mL·min$^{-1}$. The transfer line temperature of the mass spectral unit is taken place at 200° C. The chromatogram results for the detected products are studied using LabSolution software with system control.

Catalytic Optimization

The homo dinuclear VO-complex catalyst was evaluated in the aerobic oxidation of benzyl alcohol. The homogeneous catalyst (VO-complex) was entered in the redox systems of benzyl alcohol (as standard alcohol for such an oxygenation system) using an aqueous $H_2O_2$ under aerobic conditions. The effectiveness is elucidated by the obtained percentages of conversion, chemoselectivity, and yield (productivity) of the target product (i.e., benzaldehyde), (Scheme 3):

Scheme 3. The benzyl alcohol redox system using $H_2O_2$ catalyzed by VO-complex catalyst.

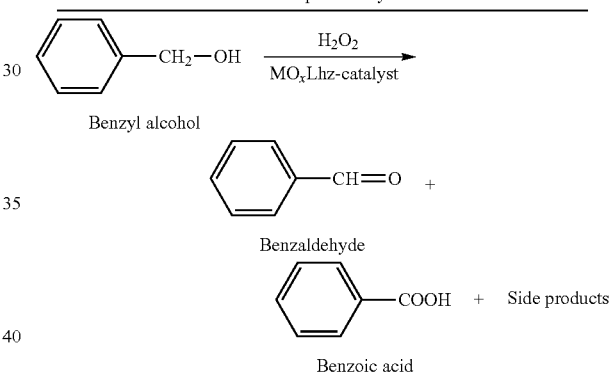

A GC-MS machine was applied to detect the amount of yielding product as reported in Table 2. Also, TON (turnover number) and TOF (turnover frequency) values were calculated and are listed in Table 2. To determine the optimum atmospheric activity for each MLss complex catalyst, long temperatures (25, 30, 40 and 50° C.) were applied for a long-monitored time of up to 6 h.

TABLE 2

The catalytic action of VO-complex in the redox system of benzyl alcohol within an aqueous $H_2O_2$ at various temperature and time.

| | | | Yielding (%)$^b$ | | | | | | |
|---|---|---|---|---|---|---|---|---|---|
| Entry$^a$ | Temp. (° C.) | Time (h) | Benzyl alc. | Benzaldehyde | Benzoic acid | Side products | Conversion (%) | Selectivity (%) | TON$^e$ | TOF$^d$ |
| 1 | 25 | 0.5 | 64 | 35 | 1 | 0 | 36 | 97 | 70 | 140 |
| 2 | | 1 | 24 | 72 | 1 | 0 | 76 | 95 | 144 | 144 |
| 3 | | 1.5 | 0 | 90 | 8 | 2 | 100 | 90 | 184 | 122 |
| 4 | | 2 | 0 | 87 | 10 | 3 | 100 | 87 | 174 | 87 |
| 5 | | 2.5 | 0 | 70 | 22 | 8 | 100 | 70 | 140 | 56 |
| 6 | | 3 | 0 | 62 | 29 | 9 | 100 | 62 | 124 | 41 |
| 7 | 30 | 0.5 | 55 | 42 | 3 | 0 | 45 | 93 | 84 | 168 |
| 8 | | 1 | 21 | 70 | 6 | 3 | 79 | 89 | 140 | 140 |
| 9 | | 1.5 | 1 | 82 | 11 | 7 | 99 | 82 | 164 | 109 |

TABLE 2-continued

The catalytic action of VO-complex in the redox system of benzyl alcohol within an aqueous $H_2O_2$ at various temperature and time.

| Entry[a] | Temp. (° C.) | Time (h) | Benzyl alc. | Yielding (%)[b] Benzaldehyde | Benzoic acid | Side products | Conversion (%) | Selectivity (%) | TON[e] | TOF[d] |
|---|---|---|---|---|---|---|---|---|---|---|
| 10 | | 2 | 0 | 72 | 19 | 9 | 100 | 72 | 144 | 72 |
| 11 | | 2.5 | 0 | 64 | 25 | 11 | 100 | 64 | 128 | 51 |
| 12 | | 3 | 0 | 53 | 32 | 15 | 100 | 53 | 106 | 35 |
| 13 | 40 | 0.5 | 39 | 55 | 5 | 1 | 61 | 90 | 110 | 220 |
| 14 | | 1 | 18 | 62 | 15 | 5 | 82 | 76 | 124 | 124 |
| 15 | | 1.5 | 3 | 75 | 22 | 7 | 97 | 72 | 150 | 100 |
| 16 | | 7 | 0 | 70 | 23 | 7 | 100 | 70 | 140 | 70 |
| 17 | | 2.5 | 0 | 53 | 35 | 12 | 100 | 53 | 106 | 42 |
| 18 | | 3 | 0 | 41 | 44 | 15 | 100 | 41 | 82 | 27 |

[a]1.0 mmol (benzyl alcohol) in 10 mL acetonitrile + 0.005 mmol VO-cmplex – 3.00 mmol $H_2O_2$ at 25. 30 or 40° C.
[b]Percentage of selective product (benzaldehyde) + benzoic acid is detected by GC/MS.
[e]TON. turnover number. refers to ratio of mmoles of selected product/mmoles of VO-catalyst.
[d]TOF. turnover frequency. refers to turnover number/time (mmol$^{-1}$ · h$^{-1}$).

Optimum Control

With the variation of the given long termed time (1-6 h) and temperature (25-40° C.), the optimum conditions for the homogeneous VO-complex catalyst are estimated and recorded, as shown in Table 2. Particularly, for the conditions of the middle reaction temperature, 25° C. (middle reaction temperature is 30 C; I think they mean middle entry of lowest reaction T of 25 C—see following), the VO-complex catalyst recorded the optimized effectiveness, as noticed by the high percentages of yielding, chemoselectivity, and the percentage of conversion with 1.5 h (entry 3, Table 2). The yield of benzaldehyde was obtained as 90% after 1.5 h with conversion and selectivity percentages of 100% and 90%, respectively.

Seemingly, at higher temperatures, 30 and 40° C., a considerable diminishing of the catalytic selectivity of VO-catalyst for the oxy-product was recorded with an observable increase of the conversion and the amounts of side products yields (i.e., benzoic acid and unknown products) for the rest reaction times (entries 7-18, Table 2).

According to the above expertise, the VO-complex catalyst demonstrated excellent catalytic efficiency compared to that of similar reported ones based on the percentages of the desired product, the optimal temperature, and the running time (Table 2). The optimized catalytic variation among the reported metal complex catalysts could be interpreted by the difference in their electronic effect of the M 2+ ions according to the improved Lewis acidic character and their electronegative feature in their homogeneous catalysts.

The high oxidation number of the central $V^{4+}$ ion in the VO-catalyst could be the main reason for its excellent catalytic potential, in which the high oxidation number of $VO^{2+}$ ions progresses the interchanging of oxidation states between $V^{4+}$ and V+5 ion. Additionally, the high reversibility of the electrochemical properties the high affinity of $VO^{2+}$ ions toward oxygenation reactions were observed. The coordinated acetylacetonate anion in its current VO-catalyst could promote their reactivity within the substitution reaction by benzyl alcohol molecules and/or the oxidant molecule, as discussed previously. On the other hand, VO-complex catalyst shows high efficiency at low reaction temperature (25° C.), which could be interpreted by the high affinity, more Lewis acid feature, and also smaller ionic radii of $V^{4+}$ ion for enhanced oxidation interchanging in the homogeneous catalyst. Distinguished reversibility of the electrochemical characteristics of $VO^{2+}$ ion was found in its complex catalyst.

Catalyst Amount Effect

Within a homogeneous aerobic atmosphere, the effect of catalyst amount can be explored by applying various mmoles of VO-complex catalysts in the reaction media. The 0.001, 0.002, 0.005, 0.01, 0.02, and 0.05 mmoles of the complex catalyst were employed at the optimized atmosphere for the catalyst. From the collected results in Table 3, the best-required amount of the loaded catalyst of VO-complex is 0.005 mmol, with the highest yielding selectivity percentages. The less loaded amounts of both catalysts (0.001 and 0.002 mmol) lead to less yielding and selectivity, as observed in Table 3.

Noticeably, for the larger amounts of the loaded catalysts (0.01, 0.02, and 0.05 mmol), the conversion percentages progressed and increased obviously, but the yielding amount and selectivity percentages were reduced (Table 3). Consequently, the reactivity of the current catalyst improved remarkably by increasing their loaded amounts to 0.005 mmoles. After that, the reactivity is enhanced with less selectivity. Clearly, the presence of two central metal ions ($V^{4+}$ ion) in the catalyst complex gave an improvement of the homo dinuclear catalyst reactivity with less loaded amounts of the catalysts, time, and temperature compared to the other reported catalysts of mononuclear ones with a novelty.

TABLE 3

Oxidation system of benzyl alcohol by $H_2O_2$ depending on the catalyst amounts catalyzed by VO-complex catalyst at the optimized conditions.

| [a]Amount, mmoles | Amount (%)[b] | | | | Conversion (%) | Selectivity (%) | TON[c] | TOF[d] |
|---|---|---|---|---|---|---|---|---|
| | Benzyl alcohol | Benzaldehyde | Benzoic acid | Side products | | | | |
| 0.001 | 31 | 66 | 3 | 0 | 69 | 96 | 132 | 26.4 |
| 0.002 | 14 | 82 | 3 | 1 | 86 | 95 | 164 | 32.8 |
| 0.005 | 0 | 90 | 8 | 2 | 100 | 90 | 184 | 122 |
| 0.01 | 0 | 83 | 11 | 6 | 100 | 83 | 166 | 33.2 |
| 0.02 | 0 | 79 | 14 | 7 | 100 | 79 | 158 | 31.6 |
| 0.05 | 0 | 45 | 42 | 13 | 100 | 45 | 90 | 18 |

[a]1.0 mmol (benzyl alcohol) and various mmol VO-catalyst in 10 mL in 10 mL acetonitrile, then 3.0 mmol an aqueous $H_2O_2$ is added, at the optimized atmosphere.
[b]Percentage of selective product (benzaldehyde) + benzoic acid is detected by GC/MS.
[c]TON, turnover number, refers to ratio of mmoles of selected product/mmoles of VO-complex catalyst.
[d]TOF, turnover frequency, refers to turnover number/time (mmol$^{-1}$ · h$^{-1}$).

Solvent Effect

Within a homogeneous aerobic atmosphere, the effect of the solvent can be explored by applying various solvents in the reaction media. Besides acetonitrile, chloroform, water, and under solvent-free conditions were employed in the optimized atmosphere for the VO-catalyst, as studied previously. From the collected results in Table 4, acetonitrile is the best solvent of the current redox reactions, with its high renitent for oxygenation, even at high reaction temperatures. As shown in the mechanistic pathway, the high polar feature and dipole moment of acetonitrile could enhance the oxygen transfer step.

Noticeably, solvent-free conditions were the optimized media for such an oxidation process with VO-complex catalyst (awarding 94% of the selective product, benzaldehyde). Chloroform exhibited a considerable advancement but less than that with acetonitrile and under solvent-free conditions (Table 4) yielding a percentage 79% of benzaldehyde. In $H_2O$, the VO-complex catalyst represents less action toward the oxidation of benzyl alcohol to benzaldehyde, yielding 66% with less selectivity and conversion. Miscible properties of benzyl alcohol to VO-complex catalyst in the applicable solvent ($H_2O$) could be lowered due to their alternative polar nature. Consequently, the solvent effect could be considered in the catalytic system with its participation in the reaction mechanism.

Catalytic Activity Comparison with the Reported Mononuclear VO-Complex Catalysts A comparison in the catalytic activity of the optimization of the most closed reported mononuclear complex catalysts in the oxidation of benzyl alcohol was conducted. All the reported mononuclear oxovanadium (IV) complex catalysts have displayed hard conditions, i.e., high reaction temperature (70-120° C.) and long running time (2-24 h) for the optimization. Furthermore, all the reported mononuclear oxovanadium (IV) complex catalysts represented less catalytic efficiency with less yield of the selective product (benzaldehyde) of the benzyl alcohol oxidation processes. Comparatively, the current dinuclear VO(IV)-complex catalyst reported its optimization at 25° C., i.e., room temperature, with a savings of required energy and heat for the accomplishment of the benzyl alcohol oxidation by $H_2O_2$. The highest yield of benzaldehyde was 90% compared to those from the mononuclear VO-complex catalysts.

Example 5—Catalytic Oxidation of Thiophene-2,5-Diamine

The novel catalytic process for the oxidation of thiophene-2,5-diamine, as the first successful trial to oxidize thiophene-2,5-diamine was investigated by aqueous $H_2O_2$ catalyzed by the present VO-complex, homogeneously at room temperature, for 40 min. The highest selective product, which was obtained in the highest scale, is 2,5-dinitrosothiophene-1-oxide with 33% yield (Scheme 4).

TABLE 4

Oxidation system of benzyl alcohol by $H_2O_2$ depending on the solvent nature catalyzed by VO-complex catalyst.

| Solvent[a] | Amount (%)[b] | | | | Conversion (%) | Selectivity (%) | TON | TOF |
|---|---|---|---|---|---|---|---|---|
| | Benzyl alcohol | Benzaldehyde | Benzoic acid | Side products | | | | |
| Acetonitrile | 0 | 90 | 8 | 2 | 100 | 90 | 184 | 122 |
| Solvent-free | 0 | 94 | 4 | 2 | 88 | 92 | 40.5 | 20.3 |
| Chloroform | 11 | 79 | 8 | 2 | 92 | 87 | 40.0 | 20.0 |
| $H_2O$ | 15 | 66 | 13 | 6 | 85 | 78 | 33.0 | 16.5 |

[a]1.0 mmol (benzyl alcohol) and 0.005 mmol VO-complex catalyst in 10 mL solvent (or in solvent-free conditions), then 3.0 mmol an aqueous $H_2O_2$ is added, at the optimized atmosphere.
[b]Percentage of selective product (benzaldehyde) + benzoic acid is detected by GC/MS.
[c]TON, turnover number, refers to ratio of mmoles of selected product/mmoles of VO-complex.
[d]TOF, turnover frequency, refers to turnover number/time (mmol$^{-1}$ · h$^{-1}$).

Scheme 4. The redox system of thiophene-2,5-diamine using $H_2O_2$ catalyzed by VO-complex catalyst.

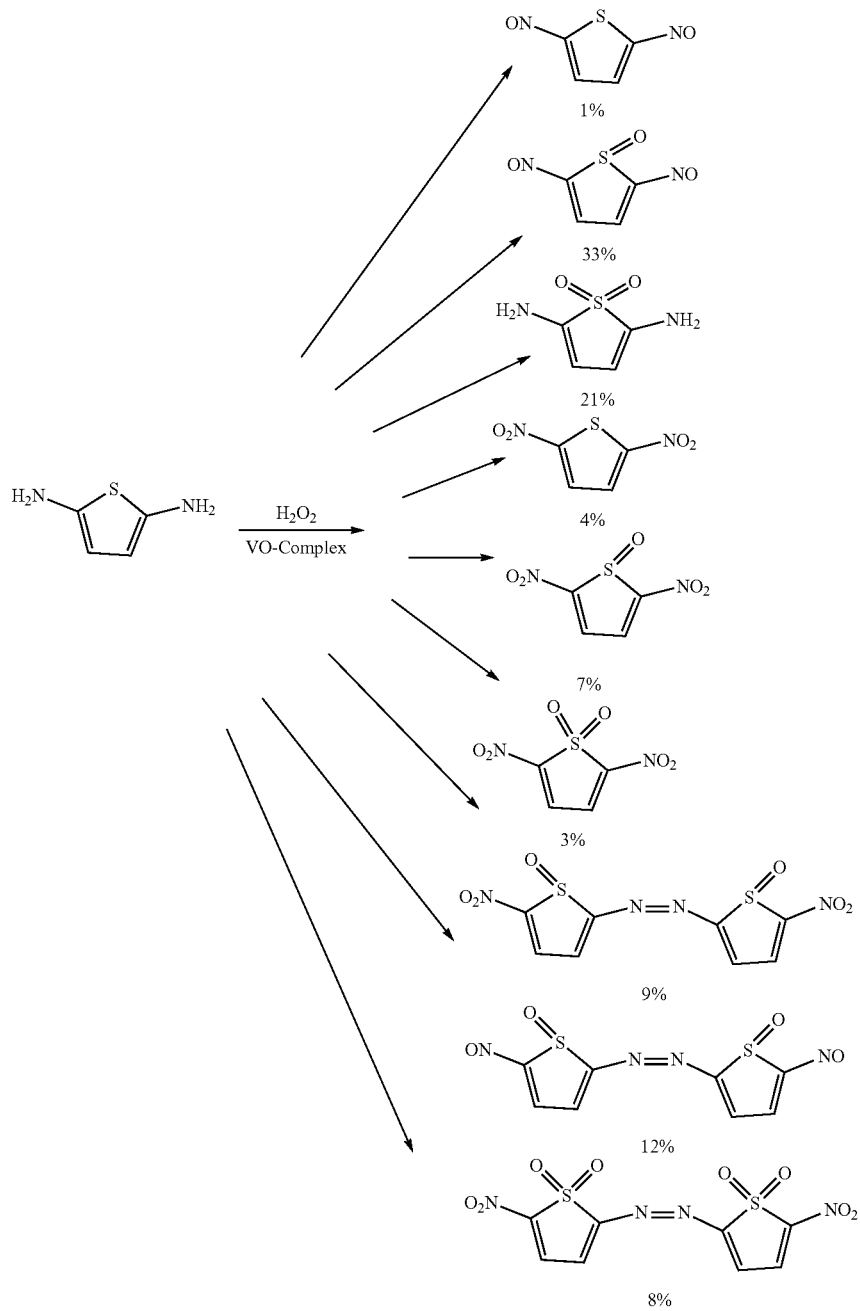

It is to be understood that the present structures, their method(s) of synthesis, and uses are not limited to the specific embodiments or examples described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A VO-diisatin succinyldihydrazone complex, said complex having the following structure:

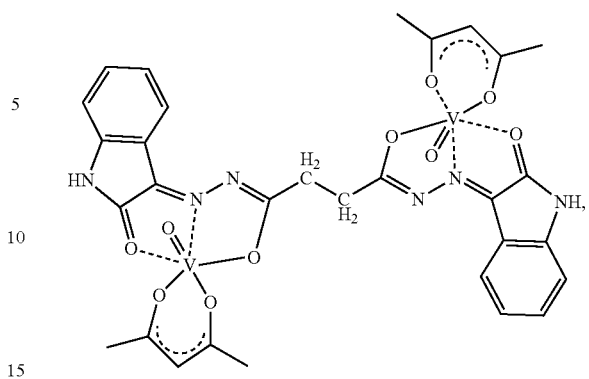

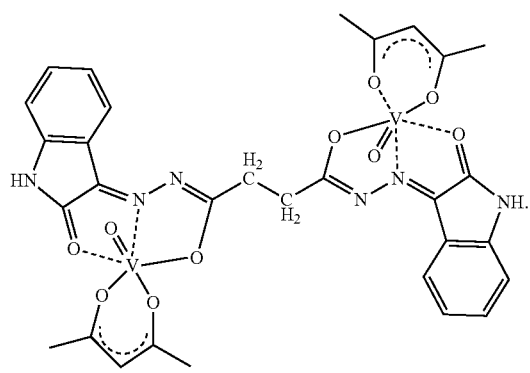

2. A method of making the VO-diisatin succinyldihydrazone complex of claim 1 having the following structure, the method comprising mixing a diisatin succinyldihydrazone ligand having the following structure

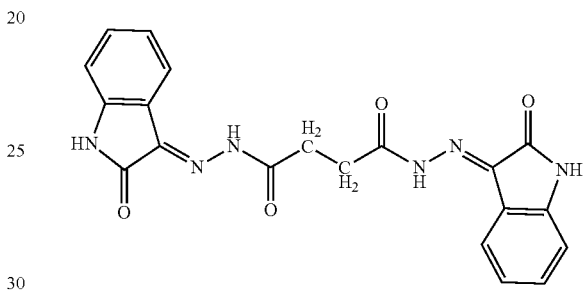

with VO(acac)$_2$ (vanadyl acetylacetonate) in methanol to form the VO-diisatin succinyldihydrazone complex by the following reaction scheme:

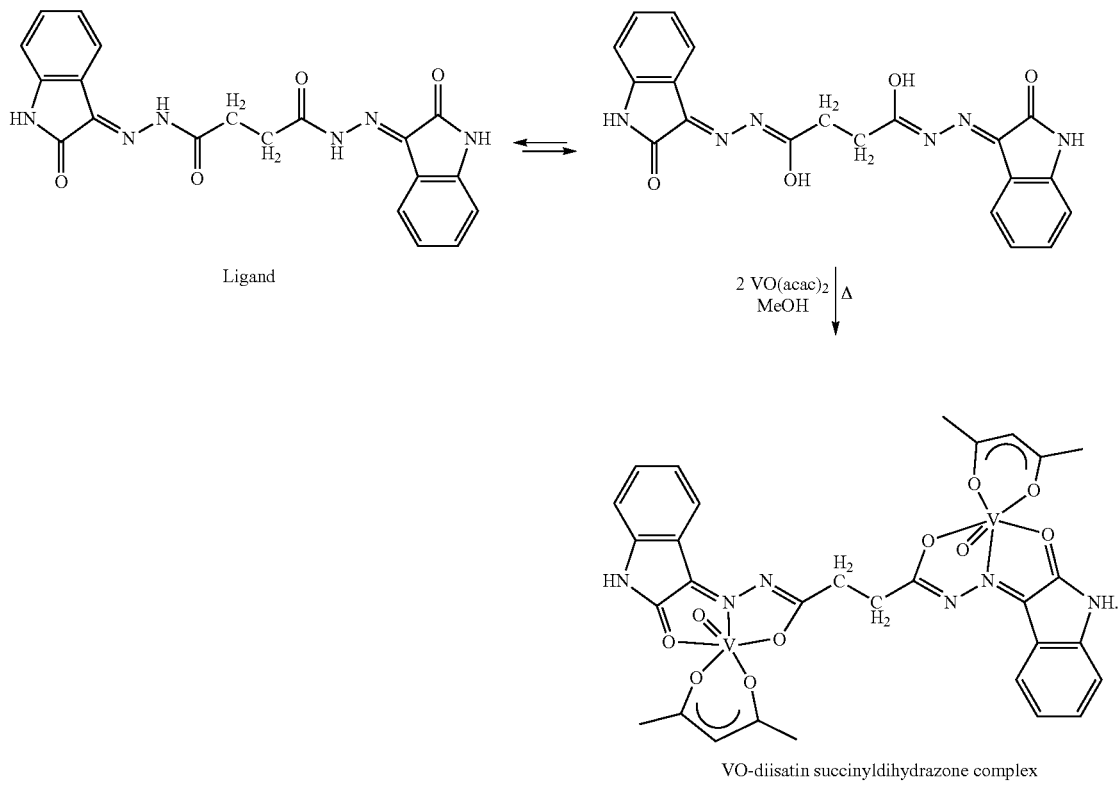

VO-diisatin succinyldihydrazone complex

3. The method of claim 2, further comprising:
pouring the diisatin succinyldihydrazone ligand in methanol into the VO(acac)$_2$ (vanadyl acetylacetonate) in methanol to form a complexing reaction mixture, and
stirring and refluxing the mixture for about 4 h at about 80° C.

4. The method of claim 3, further comprising:
bubbling nitrogen (N$_2$) gas through the complexing reaction mixture,
extracting MeOH from the complexing reaction mixture to produce a solid complex, and
aggregating the solid complex by washing with diethyl ether to produce an aggregated solid complex.

5. The method of claim 4, further comprising:
recrystallizing the aggregated solid complex in methanol to obtain the VO-diisatin succinyldihydrazone complex as a powder.

6. A method of catalyzing aerobic oxidation of an alcohol, the method comprising:
contacting the VO-diisatin succinyldihydrazone complex of claim 1 with the alcohol in the presence of aqueous H$_2$O$_2$; and
obtaining a corresponding aldehyde and acid,
wherein the VO-diisatin succinyldihydrazone complex reduces the time and the temperature required to carry out the aerobic oxidation of the alcohol.

7. The method of claim 6, wherein the alcohol is benzyl alcohol, the aldehyde is benzaldehyde, and the acid is benzoic acid, wherein an about 90% yield of the benzaldehyde is obtained.

8. A method of catalyzing aerobic oxidation of thiophene-2,5-diamine, the method comprising:
contacting the VO-diisatin succinyldihydrazone complex catalyst of claim 1 with the thiophene-2,5-diamine in the presence of aqueous H$_2$O$_2$ at room temperature; and
obtaining a corresponding 2,5-dinitrosothiophene-1-oxide.

9. The method of claim 8, wherein an about 33% yield of the 2,5-dinitrosothiophene-1-oxide is obtained.

* * * * *